(12) United States Patent
Hartwig et al.

(10) Patent No.: US 9,452,959 B2
(45) Date of Patent: Sep. 27, 2016

(54) FLUORINATION OF ARYL COMPOUNDS

(71) Applicant: THE REGENTS OF THE UNIVERSITY OF CALIFORNIA, Oakland, CA (US)

(72) Inventors: John Hartwig, Berkeley, CA (US); Patrick Fier, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/407,060

(22) PCT Filed: Jun. 12, 2013

(86) PCT No.: PCT/US2013/045449
§ 371 (c)(1),
(2) Date: Dec. 10, 2014

(87) PCT Pub. No.: WO2013/188554
PCT Pub. Date: Dec. 19, 2013

(65) Prior Publication Data
US 2015/0175508 A1    Jun. 25, 2015

Related U.S. Application Data

(60) Provisional application No. 61/658,818, filed on Jun. 12, 2012.

(51) Int. Cl.
*C07C 25/00* (2006.01)
*C07C 17/20* (2006.01)
(Continued)

(52) U.S. Cl.
CPC .......... *C07C 17/202* (2013.01); *B01J 31/1805* (2013.01); *C07C 17/208* (2013.01); *C07C 25/00* (2013.01); *C07F 1/005* (2013.01);
(Continued)

(58) Field of Classification Search
CPC ... C07C 17/20; C07C 17/202; C07C 17/204; C07C 17/206; C07C 17/208
See application file for complete search history.

(56) References Cited

U.S. PATENT DOCUMENTS 7,202,388 B2 * 4/2007 Grushin .................. C07B 39/00
570/147
2011/0015401 A1 * 1/2011 Buchwald ............. C07C 17/208
548/103

FOREIGN PATENT DOCUMENTS

WO    WO 2013/188554 A1    12/2013

OTHER PUBLICATIONS

Casitas, A. et al. J. Am. Chem. Soc. 2011, 133, 19386-19392 and S1-S52.*

(Continued)

*Primary Examiner* — Fereydoun G Sajjadi
*Assistant Examiner* — Medhanit Bahta
(74) *Attorney, Agent, or Firm* — Morgan, Lewis & Bockius LLP; Jeffry S. Mann

(57) ABSTRACT

The invention provides compositions and methods of using the compositions in fluorinating aryl precursors containing a leaving group replaceable by fluoride ion. The compositions include a metal ion source, a fluoride ion source, and a compound, which is an aryl precursor of the aryl fluoride, and which has a leaving group replaceable by the fluoride. Exemplary methods of the invention make use of such compositions and methods to prepare an aryl fluoride compound. In an exemplary embodiment, the fluoride ion source is a source of $^{18}F$.

16 Claims, 3 Drawing Sheets

(51) Int. Cl.
*B01J 31/18* (2006.01)
*C07F 1/00* (2006.01)

(52) U.S. Cl.
CPC ............ *C07C 17/20* (2013.01); *C07C 17/204* (2013.01); *C07C 17/206* (2013.01)

(56) References Cited

OTHER PUBLICATIONS

Sheppard, T. D. Org. Biomol. Chem. 2009, 7, 1043-1052.*
Adams, D. and Clark, James, "Nucleophilic routes to selectively fluorinated aromatics." *Chem. Soc. Rev.*, vol. 28, pp. 225-231 (1999).
Anbarasan, P. et al., "Efficient Synthesis of Aryl Fluorides." *Agnew. Chem.*, vol. 122, pp. 2265-2268 (2010).
Fier, P. and Hartwig, J., "Copper-Meditated Fluorination of Aryl Iodides." *J. Am. Chem. Soc.*, vol. 134, pp. 10795-10798 (2012).
Furuya, T. et al., "Palladium-Mediated Fluorination of Arylboronic Acids." *Angew. Chem. Int. Ed.*, vol. 47, pp. 5993-5996 (2008).
Furuya, T. et al., "Silver-Mediated Fluorination of Functionalized Aryl Stannanes," *J. Am Chem. Soc.*, vol. 131, pp. 1662-1663 (2009).
Furuya, T. and Ritter, T., "Fluorination of Boronic Acids Mediated by Silver(I) Triflate." *Organic Letters*, vol. 11, No. 13, pp. 2860-2863 (2009).
Furuya, T. et al., "Catalysis for Fluorination and Trifluoromethylation." *Nature*, vol. 473, pp. 470-477 (2011),.
Olah, G. et al., "Synthetic Methods and Reactions, 63. Pyridinium Poly(hydrogen fluoride) (30% Pyridine-70% Hydrogen Fluoride): A Convenient Reagent for Organic Fluorination Reactions." *J. Org. Chem.*, vol. 44, No. 22 pp. 3872-3881 (1979).
Tang, P. et al., "Silver-Catalyzed Late-Stage Fluorination." *J. Am. Chem. Soc.*, vol. 132, No. 34, pp. 12150-12154 (2010).
Tang, P. et al., "Deoxyfluorination of Phenols," *J. Am. Chem. Soc.*, vol. 133, No. 30, pp. 11482-11484 (2011).
Tang, P. and Ritter, T., "Silver-mediated fluorniation of aryl silanes." *Tetrahedron*, vol. 67, No. 24, pp. 4449-4454 (2011).
Watson, D. et al., "Formation of ArF from LPdAr(F): Catalytic Conversion of Aryl Triflates to Aryl Fluorides." *Science*, vol. 325, pp. 1661-1664 (2009).
Weng, Z. et al., "Cooperative Effect of Silver in Copper-Catalyzed Trifluoromethylation of Aryl Iodides Using $Me_3SiCF_3$." *Organometallics*, vol. 30, pp. 3229-3232 (2011).

* cited by examiner

FLUORINATION OF ARYL COMPOUNDS

CROSS REFERENCE TO RELATED APPLICATIONS

This application is a 371 of PCT/US13/45449 filed Jun. 12, 2013 which claims benefit of U.S. Provisional Application No. 61/658,818 filed on Jun. 12, 2012, both of which are incorporated herein by reference in their entireties.

STATEMENT AS TO RIGHTS TO INVENTIONS MADE UNDER FEDERALLY SPONSORED RESEARCH OR DEVELOPMENT

This invention was made with Government support under Grant Number R37GM055382-14, awarded by the National Institutes of Health. The Government has certain rights in the invention.

BACKGROUND OF THE INVENTION

The unique stability, reactivity and biological properties of fluorinated compounds make them useful in many chemical disciplines. Compounds containing an aryl fluoride moiety are common in pharmaceuticals and agrochemicals because the site containing fluorine is stable toward degradation, and this stability improves biological activity.

The conditions typically used to form aryl-fluorine bonds are harsh; thus the fluorine is usually introduced into the arene ring at the beginning of a synthesis or as part of a building block. Improved methods for late-stage aromatic fluorination would be important for diversification in medicinal chemistry. Moreover, methods for aromatic fluorination with simple fluoride sources would be valuable for the preparation of $^{18}F$ labeled compounds used in PET imaging. Yet, no general method has been reported for the fluorination of aryl halides.

Instead, aryl fluorides have been prepared by the Balz-Schiemann reaction involving the decomposition of aryldiazonium salts (Scheme 1) (Olah, et al., *J. Org. Chem.*, 44:3872 (1979)). The acidic conditions, the toxicity of the reagents, and the potential for explosions limit the synthetic utility of the Balz-Schiemann reaction (Olah, et al., *J. Org. Chem.*, 44:3872 (1979)). Alternatively, aryl fluorides bearing electron-withdrawing groups have been prepared by the halogen exchange (halex) process in which electron deficient aryl chlorides or nitroarenes undergo nucleophilic aromatic substitution with fluoride at high temperatures (Scheme 1) (Adams, et al., *Chem. Soc. Rev.*, 28:225 (1999)). However, this reaction occurs only with substrates that are activated toward nucleophilic attack.

Recently, transition metal complexes have been used to prepare fluoroarenes (Furuya, et al., *Nature*, 473:470 (2011)). Palladium-catalyzed fluorination of aryl triflates has been reported (Scheme 2) (Watson, et al., *Science*, 325:1661 (2009)). Although these findings demonstrated that aryl electrophiles can undergo fluorination in the presence of a transition metal catalyst, the formation of a single product occurred only with substrates bearing electron-withdrawing groups (Watson, et al., *Science*, 325:1661 (2009)). The triflates for this reaction are formed from phenols, and a reagent for the conversion of phenols to aryl fluorides was reported more recently (Tang, et al., *J. Am. Chem. Soc.*, 133:11482 (2011)). Methods for the conversion of aryl stannanes (Furuya, et al., *J. Am. Chem. Soc.*, 131:1662 (2009); and Tang, et al., *J. Am. Chem. Soc.*, 132:12150 (2010)), boronic acids (Furuya, et al., *Angew. Chem. Int. Edit.*, 47:5993 (2008); and Furuya, et al., *Org. Lett.*, 11:2860 (2009)), and silanes (Tang, et al., *Tetrahedron*, 67:4449 (2011)) to aryl fluorides with silver or palladium and an electrophilic fluoride source also have been published, but the aryl nucleophiles in these reactions are often prepared from the aryl halide, and therefore a method to convert aryl halides to the corresponding aryl fluorides would be more direct than the reactions of main group-aryl reagents.

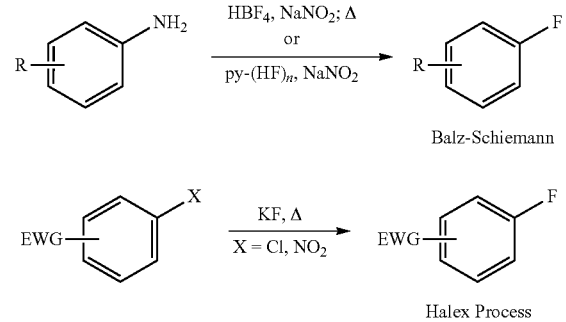

Scheme 1. Conventional Routes to Fluoroarenes

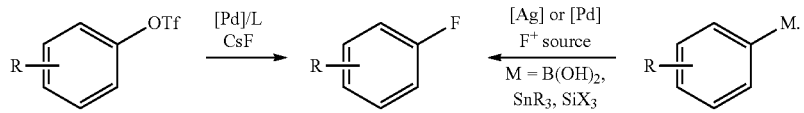

Scheme 2. Metal Mediated Aryl Fluorination.

Casitas et al. have published a method of performing a copper-mediated halide exchange reaction on an aryl halide precursor substituted with a nitrogen-containing macrocyle, having three amine moieties, which chelates the copper. The results achieved by these workers are limited to such chelating precursors. *J. Am. Chem. Soc.* 2011, 122, 19386-19392.

Accordingly, a reaction that directly fluorinates an aryl precursor to form the corresponding aryl fluoride at low to modest temperatures (e.g., <300° C.) would represent a significant advance in the art of aryl fluorination and the provision of aryl fluorides. Further, such a reaction that does not require the presence of electron withdrawing substituents on the aryl nucleus would also be of value. Surprisingly, the present invention provides such a reaction and compositions of use in carrying out this reaction.

BRIEF SUMMARY OF THE INVENTION

The present invention provides compositions and methods for fluorinating functionally diverse aryl precursor compounds with a simple metal reagent and fluoride source. In various embodiments, the metal is complexed with a ligand and the rapid decomposition of the metal fluoride is avoided. The reaction occurs at low to modest temperatures, allowing the presence of diverse substituents on the aryl nucleus. Furthermore, the presence of electron withdrawing substituents on the aryl ring is not required.

In general terms, the invention provides a method of aryl fluorination and compositions of use therein:

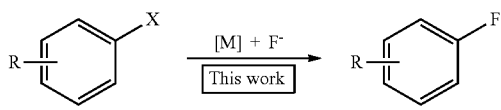

in which X is a leaving group, M is a metal and F— is a fluoride ion source. In an exemplary embodiment, [M] is a liganded copper ion.

The invention provides an operationally simple fluorination of aryl precursor compounds with readily available reagents. This reaction tolerates a range of functional groups other than the leaving group, e.g., ether, amide, ester, ketone, and aldehyde functional groups and occurs with heterocyclic systems. Moreover, it occurs in high yield with sterically hindered aryl precursor compounds. Also provided are compositions and methods for the synthesis of $^{18}F$ labeled compounds, which, in an exemplary embodiment, are of use in PET imaging.

Thus, in an exemplary embodiment, there is provided a reaction mixture for fluorinating an aryl compound having a leaving group. The reaction mixture includes: (i) the aryl precursor compound, which is optionally further substituted at one or more positions other than the position occupied by the leaving group; (ii) a fluoride ion source; and (ii) a metal source, wherein the metal ion source mediates fluorinating the aryl precursor at the position of the leaving group with a fluoride ion derived from the fluoride ion source. In an exemplary embodiment, the precursor is not substituted with a nitrogen-containing macrocycle, e.g., a chelating macrocycle with three amine moieties, such as that disclosed by Casitas et al., supra.

Also provided is a method of fluorinating an aryl precursor compound having a leaving group, which is replaceable by fluoride from a fluoride ion source. The method includes forming a reaction mixture according to the invention and incubating the reaction mixture under conditions appropriate to form said fluoroaryl compound.

Other exemplary objects, advantages and aspects of the invention are set forth in the detailed description that follows.

DETAILED DESCRIPTION OF THE INVENTION

I. Introduction

Figure 1:
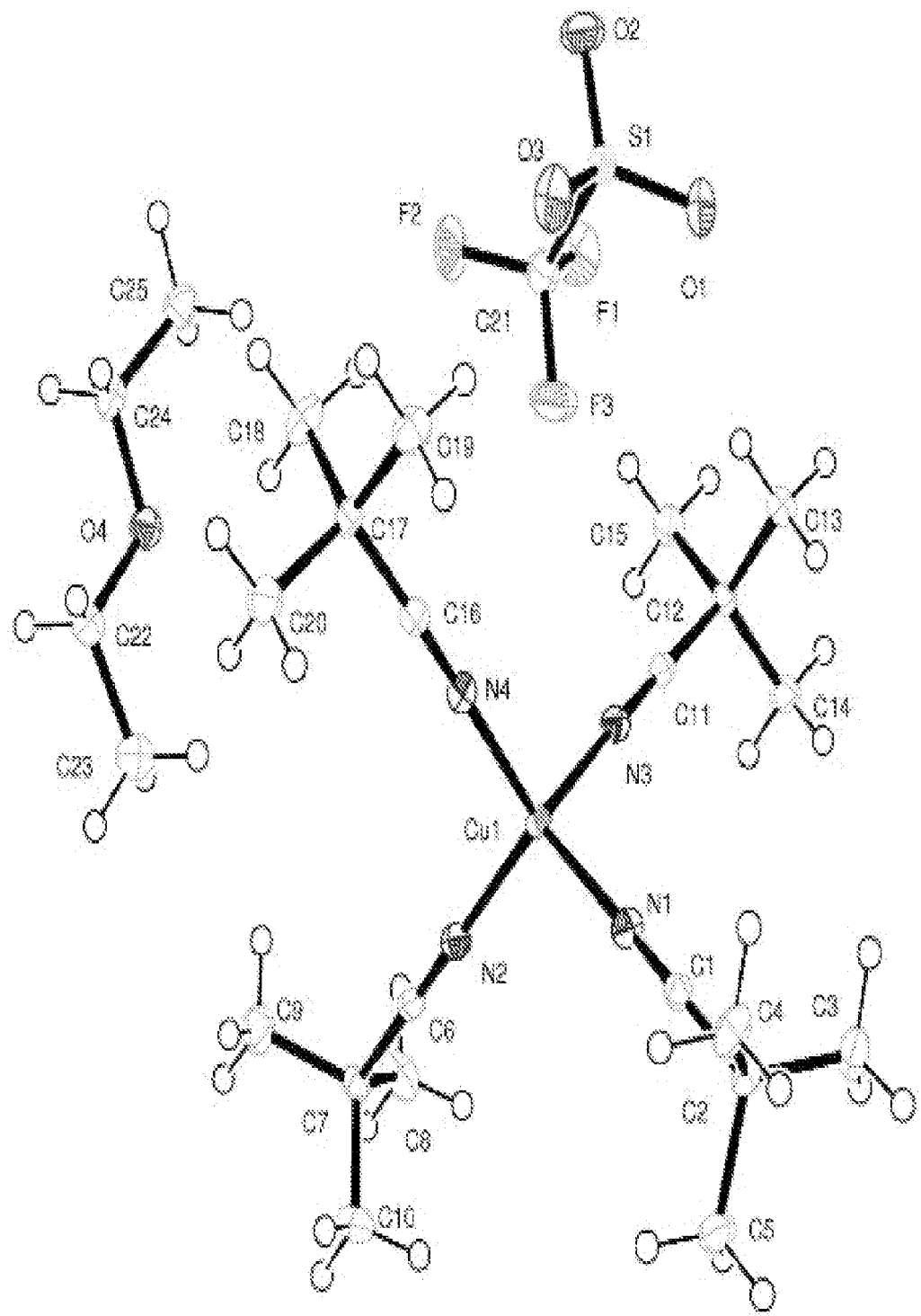
FIG. 1 is an x-ray crystal structure of (tBuCN)$_4$CuOTf.
Figure 2A:
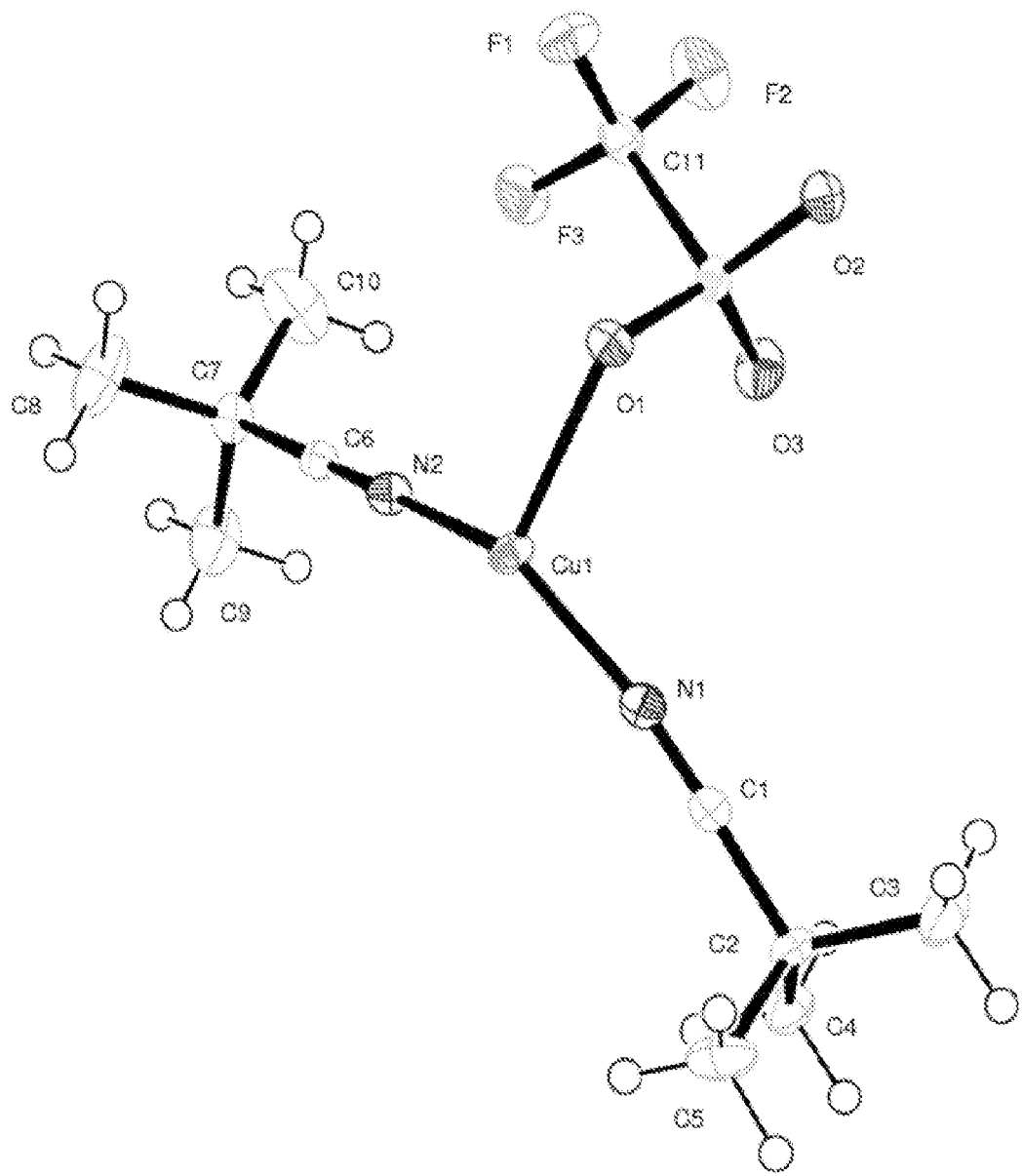
FIG. 2A is an x-ray crystal structure of the monomer unit of (tBuCN)$_2$CuOTf.
Figure 2B:
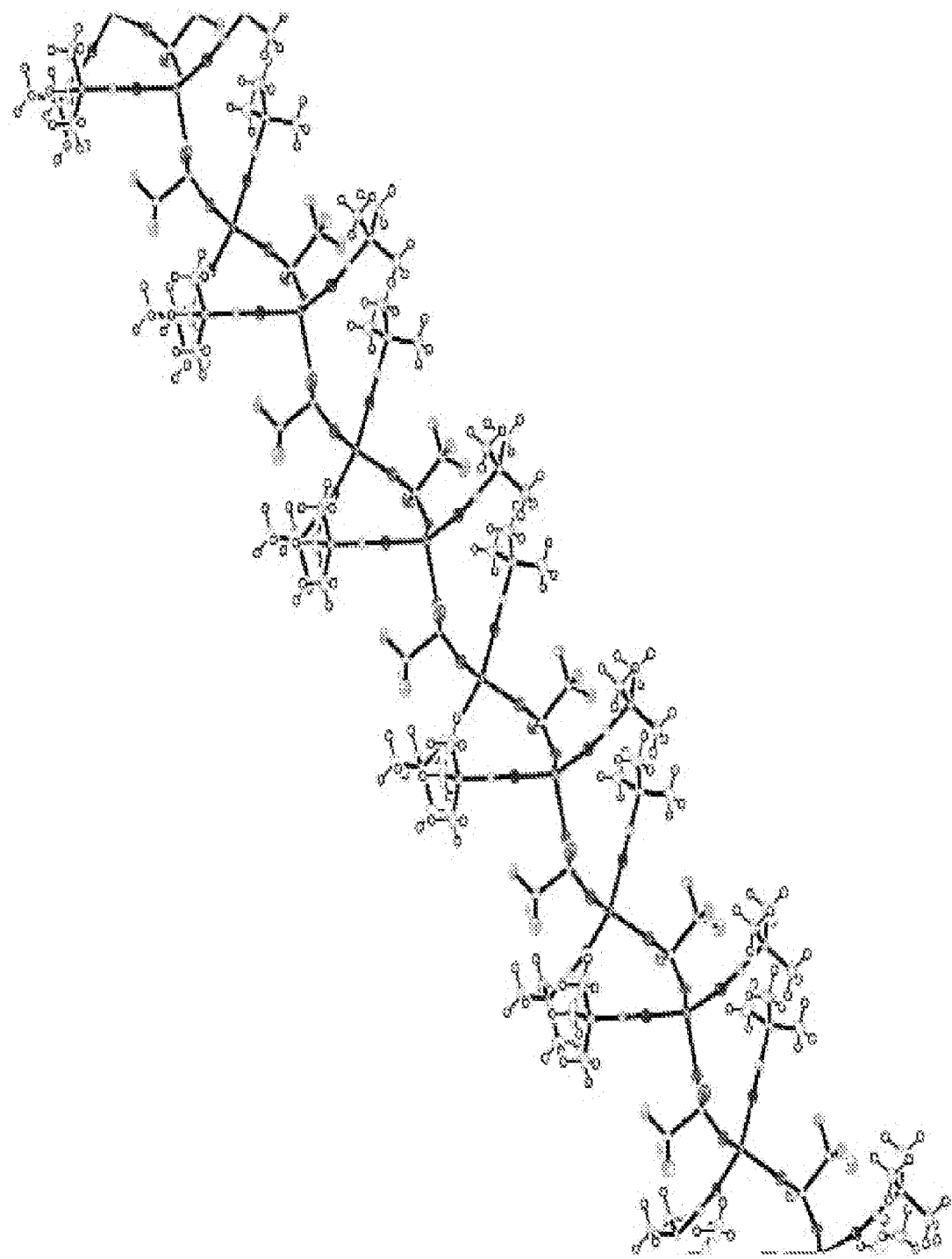
FIG. 2B is an x-ray crystal structure of (tBuCN)$_2$CuOTf showing the polymeric structure.

The ability to selectively fluorinate an aryl substrate has broad application, especially in the agricultural, pharmaceutical, and polymer industries. As described herein, the present invention relates to compositions and methods for transforming an aryl substrate to the corresponding fluoro compound. The compositions and methods of the invention utilize simple, readily available substrates and reaction mixtures and, thus, have wide applicability.

In various embodiments, the present invention provides a one-step procedure for the fluorination of aryl substrates that occurs with readily available and non-hazardous reagents. This reaction tolerates a wide range of substituents, e.g., amine, ether, amide, ester, aromatic bromide and protected alcohol functionalities, and occurs in high yield even with sterically hindered substrates. The simplicity and generality of this method makes it attractive for the introduction of fluoride into functionally diverse aryl compounds.

In various embodiments, there is provided a reaction mixture for fluorinating an aryl compound having a leaving group, said reaction mixture comprising: (i) the aryl precursor compound, which is optionally further substituted at one or more positions other than the position occupied by the leaving group; (ii) a fluoride ion source; and (ii) a metal source. The metal ion source mediates the fluorinating of the aryl substrate at the position of the leaving group with fluoride ion derived from the fluoride ion source.

Also provided is a method of utilizing such a reaction mixture to prepare an aryl fluoride compound. In general terms, the method includes incubating the reaction mixture under conditions sufficient to form the aryl fluoride.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10,\ 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R' and R'" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is –O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties. In exemplary embodiments of the invention, a substituted aryl or heteroaryl ring system is not substituted with a nitrogen-containing macrocycle, e.g., an amine-containing chelating macrocycle.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

A "chelating macrocycle" is a substituent bound to two or more positions on an aryl or heteroaryl core such that the two substituents form one or more ring systems. These ring systems include one or more heteroatoms (e.g., N, S, and O), which have a lone pair of electrons that will interact with a metal (e.g., copper) to form a complex. An exemplary chelating macrocycle includes 3 nitrogen moieties (a "nitrogen-containing macrocycle"), see, e.g., Casitas et al., supra.

The terms "substrate" and "precursor" are used interchangeably and refer to compound with a leaving group substitutable by a fluorine synthon in a method and composition of the invention. An exemplary substrate or precursor is an iodo-substituted aryl compound, which can react under the conditions of the invention, to yield at least one product having a fluoro moiety.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, the term "leaving group" refers to a portion of a substrate that is cleaved from the substrate in a reaction. The leaving group is an atom (or a group of atoms) that is displaced as stable species taking with it the bonding electrons. Typically the leaving group is an anion (e.g., Cl$^-$) or a neutral molecule (e.g., H$_2$O). Exemplary leaving groups include a halogen, OC(O)R$^{36}$, OP(O)R$^{36}$R$^{37}$, OS(O)R$^{36}$, and OSO$_2$R$^{36}$. R$^{36}$ and R$^{37}$ are members independently selected from substituted or unsubstituted alkyl, substituted or unsubstituted aryl, substituted or unsubstituted heteroaryl and substituted or unsubstituted heterocycloalkyl. Useful leaving groups include, but are not limited to, halides, sulfonic esters, oxonium ions, alkyl perchlorates, sulfonates, e.g., arylsulfonates, ammonioalkanesulfonate esters, and alkylfluorosulfonates, phosphates, carboxylic acid esters, carbonates, ethers, and fluorinated compounds (e.g., triflates, nonaflates, tresylates), S R$^{36}$, (R$^{36}$)$_3$P$^+$, (R$^{36}$)$_2$S$^+$, P(O)N(R$^{36}$)$_2$(R$^{36}$)$_2$, P(O)R$^{38}$R$^{36}$R$^{39}$R$^{36}$ in which each R$^{36}$ is independently selected from the members provided in this paragraph and R$^{38}$ and R$^{39}$ are each either S or O. The choice of these and other leaving groups appropriate for a particular set of reaction conditions is within the abilities of those of skill in the art (see, for example, March J, ADVANCED ORGANIC CHEMISTRY, 2nd Edition, John Wiley and Sons, 1992; Sandler S R, Karo W, ORGANIC FUNCTIONAL GROUP PREPARATIONS, 2nd Edition, Academic Press, Inc., 1983; and Wade L G, Compendium OF ORGANIC SYNTHETIC METHODS, John Wiley and Sons, 1980).

The term "ligand" has the meaning ordinarily ascribed to it in the art. Exemplary ligands include at least one donor atom capable of binding to Cu(0), Cu(I) or Cu(II). Ligands can include sterically bulky species, such as substituted or unsubstituted aryl, substituted or unsubstituted heteroaryl and substituted or unsubstituted fused ring systems, secondary and tertiary alkyl groups and the like. Exemplary ligands include, without limitation, nitrogen-containing ligands and oxygen-containing ligands (e.g., nitriles, amines, aminoalcohols, amino acids, phenols), and phosphorus-containing ligands (e.g., phosphines and phosphites).

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Below are examples of specific embodiments for carrying out the present invention. The examples are offered for illustrative purposes only, and are not intended to limit the scope of the present invention in any way.

III. The Compositions

In an exemplary embodiment, the invention provides a reaction mixture that includes an aryl precursor compound with a leaving group, the metal source (liganded or unliganded) and the fluoride ion source. In various embodiments, the reaction mixture also contains an appropriate solvent for at least one of the components of the reaction mixture.

The aryl precursor includes at least one leaving group. Useful leaving groups are conveniently selected from any such group that can be substituted by a fluoride ion or fluoride ion synthon using a reaction mixture of the invention in a method of the invention. In various embodiments, the leaving groups are selected from iodide, bromide, mesylate, tresylate, triflate, BF$_4$, PF$_6$, SbF$_6$, Triflimide (Tf$_2$N), perchlorate, tetrakis(pentafluorophenyl)borate, tetrakis(3,5-bistrifluoromethylphenyl)borate, Al(OC(CF$_3$)$_3$)$_4$, nonaflate, sulfate, fluorosulfonate, and chlorosulfonate. Other appropriate leaving groups will be apparent to those of skill in the art. In an exemplary embodiment, the leaving group is iodide.

The reaction mixture functions to transform aryl substrates of a broad range of structures to fluoroaryl compounds. For example, in addition to the leaving group, the precursor is optionally further substituted with an amine, ether, amide, ester, bromide, protected alcohol or a combination thereof. The metal mediates the transfer of the fluoride ion from the fluoride ion source to the position of the aryl ring occupied by the leaving group. In various embodiments, the precursor is not substituted with a nitrogen-containing macrocycle, e.g., a macrocycle including three amine moieties.

In an exemplary embodiment, the aryl precursor compound has the formula:

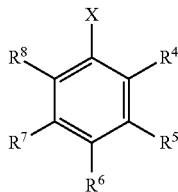

wherein $R^4$, $R^5$, $R^6$, $R^7$, and $R^8$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. In an exemplary embodiment, two or more of $R^4$, $R^5$, $R^6$, $R^7$, and $R^8$ are not joined to form at least one macrocycle. In various embodiments, two or more of these substituents are not joined to form a nitrogen-containing macrocycle. In an exemplary embodiment, $R^4$ and $R^8$ are not joined to form a macrocycle, for example, the substituents are not joined to form a nitrogen-containing macrocycle. In various embodiments, $R^4$ and $R^8$ are not joined to form the nitrogen-containing macrocycle of Casitas et al., supra.

X is a leaving group. The symbols $R^9$ and $R^{10}$ represent members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

The reaction mixture can further include a solvent and this solvent can be any compound or mixture of compounds useful to dissolve at least a portion of one or more component of the reaction mixture. In an exemplary embodiment, the solvent is DMF.

The metal source in the reaction mixture can be of any useful formula and form. In various embodiments, the metal is selected from Cr, Mn, Fe, Co, Cu, Ni, Pd, Rh, Ag and Pt. In various embodiments, the metal is Cu(0), Cu(I) or Cu(II).

In exemplary embodiments, the metal source is selected from a metal ion and a complex of a metal ion with one or more ligands. In various embodiments, the metal ion is an ion of Cu(0), Cu(I) or Cu(II). In various embodiments, the metal ion is $Cu^+$. In an exemplary embodiment, the copper ion source is CuI.

In an exemplary embodiment, the metal ion source has the formula:

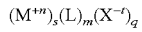

$$(M^{+n})_s(L)_m(X^{-t})_q$$

wherein M is the metal ion; L is a ligand, e.g., an organic ligand; X is an anion; and n, s, m, t and q are integers independently selected from 1, 2 and 3, such that $(s \times n)=(t \times q)$, or the such that the cationic charge(s) and anionic charge(s) are balanced and the metal source is electronically neutral.

The metal ion is any ion of use to replace a leaving group on an aryl precursor with a fluoride from the fluoride ion source. Exemplary metal ions of use in the present invention include wherein the metal ion is an ion of a member selected from Cr, Mn, Fe, Co, Cu, Ni, Pd, Rh, Ag and Pt. In an exemplary embodiment, the metal ion is Cu+.

The ligand is any ligand useful to complex the metal ion and, in an exemplary embodiment, is a substituted or unsubstituted alkyl or substituted or unsubstituted aryl nitrile ligand, RCN. R groups of various substitution patterns are of use in the ligand, reaction mixture and methods of the invention. In an exemplary embodiment, the nitrile is selected for the simplicity of its structure and/or its ready availability. For example, in one embodiment, R is an unsubstituted alkyl, e.g., unsubstituted $C_1$-$C_6$ alkyl. In various embodiments, R is selected from unsubstituted alkyl does not have an abstractable proton at a position alpha to the cyano moiety. In various embodiments, the nitrile is t-butylnitrile.

The counterion X is selected from organic and inorganic ions to form the corresponding salt. In various embodiments, X is selected from $BF_4$, $PF_6$, $SbF_6$ and OTf, Triflimide $(Tf_2N)$, perchlorate, tetrakis(pentafluorophenyl)borate, tetrakis(3,5-bistrifluoromethylphenyl)borate, $Al(OC(CF_3)_3)_4$, nonaflate, sulfate, fluorosulfonate, and chlorosulfonate.

The reaction mixture also includes a source of fluoride ion. The fluoride ion source can be any useful compound in any useful form with the proviso that it provides sufficient fluoride ion for the fluorination reaction to occur. Exemplary fluoride ion sources include salts of alkali metals, alkaline earth metals and coinage metals. In an exemplary embodiment, the fluoride ion source is AgF, CsF, KF, NaF, LiF, $R_4N^+$ $R'SiF_2^-$, $R_4P^+F^-$, and the like.

Examples of useful aryl precursors, exemplified as their iodide analogs, and of their fluoroaryl analogs are set forth in Table 1. This table also provides exemplary reactions and yields using $^tBuCN$-ligated CuOTf. This ligated copper compound can be prepared in multi-gram quantites from $Cu_2O$, triflic acid and $^tBuCN$. This complex is stable to oxygen and absorbs moisture from the air only slowly. Thus, this species can be weighed quickly on the benchtop.

The data in Table 1 show that electron-rich and electron-poor iodoarenes react to form the aryl fluorides in good yields, as determined by NMR spectroscopy. Sterically hindered aryl iodides (1h, 1i) reacted to provide nearly quantitative yields of the aryl fluoride. Esters, amides, aldehydes, ketones, and indole heterocycles were tolerated under the reaction conditions. Reactions conducted with AgF as the limiting reagent and an excess of aryl iodide provided high yields of the aryl fluoride 2m. Conditions for conducting fluorinations with limiting fluoride are important for the use of this process to provide $^{18}$F-labeled product for PET imaging. The aryl fluoride 2a was isolated in good yield on a 0.5 mmol scale.

TABLE 1

Fluorination of Aryl Iodides with ($^t$BuCN)$_2$CuOTf and AgF$^a$

R—Ar—I  →  R—Ar—F ($^t$BuCN)$_2$CuOTf (3 equiv), AgF (2 equiv), DMF, 140° C., 22 h 2a (Bu-C$_6$H$_4$-F), 74% (62%)$^b$
2b, R = Ph, 68%
2c, R = Bn, 48%
2d (Ph-C$_6$H$_4$-F), 57%
2e (1-fluoronaphthalene), 50%
2f (tBu-C$_6$H$_4$-F), 78%
2g (3,5-dimethylfluorobenzene), 68%
2h (2-methylfluorobenzene), 96% (87%)$^c$
2i (2,6-dimethylfluorobenzene), 96%
2j (F$_3$C-C$_6$H$_4$-F), 40%
2k (EtO$_2$C-C$_6$H$_4$-F), 46%
2l (Ph-C(O)-C$_6$H$_4$-F), 56%
2m (OHC-C$_6$H$_4$-F), 43% (75%)$^d$
2n, R = H, 40% (tBuC(O)N(R)-C$_6$H$_4$-F)
2o, R = Me, 62%
2p (1-(4-fluorobenzyl)indole), 59%
2q (5-fluoro-1-methylindole), 40%

$^a$Reactions were performed with 0.1 mmol of aryl iodide to determine yields by $^{19}$F NMR spectroscopy with 1-bromo-4-fluorobenzene as an internal standard added after the reaction. $^{19}$F NMR chemical shifts were compared with those of the authentic aryl fluorides.
$^b$Isolated yield from a reaction with 0.5 mmol of ArI.
$^c$Reactions were conducted with 1 eq ArI, 2 equiv of ($^t$BuCN)$_2$CuOTF and 1 equiv of of AgF.
$^d$Reactions were conducted with 3 equiv of ArI, 2 equiv of ($^t$BuCN)$_2$CuOTF and 1 equiv of AgF.

As will be appreciated by those of skill in the art, though they generically represent iodo compounds, the formulae set forth above are equally applicable to precursors substituted with a leaving group which is not an iodo moiety.

In various embodiments, the invention provides a reaction mixture in which the ratio of metal to the fluoride ion source is 1 or greater than 1. In various embodiments, the invention provides a reaction mixture in which the aryl precursor, the metal source and the fluoride ion source are present in the reaction mixture in a ratio which is from about 1:2:1 to about 1:10:2, e.g., 1:3:2, 1:5:2, 1:7:2. In an exemplary embodiment, the aryl precursor is an aryl halide (e.g., ArI) and the metal source is Cu$^+$ in liganded form. In various embodiments, the ligand is t-butyl nitrile.

The metal (e.g., copper) can be present in any amount of excess relative to the fluoride ion source. In various embodiments, the ArI:F ratio is reversed, such that the ArI to F ratio is >1. In various embodiments, this inverted ratio is used for the $^{18}$F radiolabeling of an aryl substrate.

TABLE 2

Effect of added AgOTf and CsF on the aryl iodide fluorination$^a$

Bu-C$_6$H$_4$-I →  Bu-C$_6$H$_4$-F ($^t$BuCN)$_2$CuOTf (3 equiv), AgF (2 equiv), Additive, DMF, 140° C., 22 h

| Entry | Additive | ArF (%) | ArH (%) | Conversion (%) |
|---|---|---|---|---|
| 1 | AgOTf (1 eq) | 18 | 13 | 60 |
| 2 | AgOTf (2 eq) | 5 | 22 | 51 |

TABLE 2-continued

| 3 | CsF (1 eq) | 71 | 23 | 100 |
| 4 | CsF (2 eq) | 59 | 25 | 92 |

[a]Reactions were performed with 0.1 mmol of 1a in 0.5 mL of DMF for 22 h. Yields were determined by gas chromatography with 1-bromo-4-fluorobenzene as an internal standard added after the reaction.

IV. The Methods

In various embodiments, the present invention provides methods for converting an aryl precursor compound functionalized with a leaving group to a fluoro aryl compound. In an exemplary embodiment, the method includes: (a) forming a reaction mixture as set forth herein; and (b) incubating the reaction mixture under conditions appropriate to form the fluoro aryl compound by substituting the leaving group with a F moiety derived from the fluoride ion source. In an exemplary embodiment, the leaving group is a halide moiety, e.g., an iodo moiety.

According to the method of the invention, any useful temperature or range of temperatures can be used to convert the precursor to the desired product. In various embodiments, the temperature is less than about 300° C., less than about 250° C. or less than about 200° C. In an exemplary embodiment, the reaction mixture is incubated at a temperature from about 50° C. to about 180° C., e.g., about 80° C. to about 140° C., e.g., about 120° C.

The reaction mixture can be incubated for any useful length of time. In various embodiments, the invention is incubated at a desired temperature for about 1 hour to about 36 hours, e.g., for about 6 hours to about 24 hours.

The reaction mixture can be incubated in a vessel of any useful configuration. In an exemplary embodiment, the vessel is sealed while the reaction mixture is incubated, e.g., a sealed tube.

The following examples illustrate embodiments of the invention and are not intended to limit the scope of the compositions of the invention or the methods in which they find use.

EXAMPLES

Example 1

General Experimental Details

All manipulations were conducted under an inert atmosphere with a nitrogen-filled glovebox unless otherwise noted. All reactions were conducted in oven-dried 4-mL vials fitted with a Teflon-lined screw cap under an atmosphere of nitrogen unless otherwise noted.

Silver fluoride (>99%) was purchased from Acros and used as received. N,N-Dimethylformamide (DMF), 99.8%, Extra Dry over Molecular Sieves, was purchased from Acros and used without further purification. Unless otherwise noted, all other reagents were purchased from commercial suppliers and used as received. N-(4-iodophenyl)pivalamide (1n), [1]N-(4-iodophenyl)-N-methylpivalamide (1o) (Fier, et al., *J. Am. Chem. Soc.*, 134:5524 (2012)) and 5-iodo-1-methyl-1H-indole (1q) (Rene, et al., *Org. Lett.*, 12:2116 (2010)) were prepared according to literature procedures.

NMR spectra were acquired on 400 MHz, 500 MHz, or 600 MHz Bruker instruments at the University of California. NMR spectra were processed with MestReNova 5.0 (Mestrelab Research SL). Chemical shifts are reported in ppm and referenced to residual solvent peaks ($CHCl_3$ in $CDCl_3$: 7.26 ppm for $^1H$ and 77.0 ppm for $^{13}C$) or to an external standard (1% $CFCl_3$ in $CDCl_3$: 0 ppm for $^{19}F$). Coupling constants are reported in hertz.

All GC-MS analyses were conducted with an Agilent 6890N GC equipped with an HP-5 column (25 m×0.20 mm ID×0.33 μm film) and an Agilent 5973 Mass Selective Detector. The temperature for each run was held at 50° C. for 2 min, ramped from 50° C. to 300° C. at 40° C./min, and held at 300° C. for 5 min. The effect of the nitrile, counterion and precursor ratios in an exemplary system is shown in Table 1.

TABLE 1

Effect of Nitrile, Counterion and Reagent Ratios

| Entry | RCN | X | ArI:[Cu]:AgF | yield (%) |
|---|---|---|---|---|
| 1 | MeCN | $BF_4$ | 1:1:1 | 7 |
| 2 | MeCN | $PF_6$ | 1:1:1 | 16 |
| 3 | MeCN | $SbF_6$ | 1:1:1 | 11 |
| 4 | $^iPrCN$ | $PF_6$ | 1:1:1 | 3 |
| 5 | $^iPrCN$ | $SbF_6$ | 1:1:1 | 39 |
| 6 | PhCN | $SbF_6$ | 1:1:1 | 24 |
| 7 | $^tBuCN$ | $SbF_6$ | 1:1:1 | 36 |
| 8 | $^tBuCN$ | OTf | 1:1:1 | 28 |
| 9 | $^tBuCN$ | OTf | 1:2:1 | 65 |
| 10 | $^tBuCN$ | OTf | 1:1:2 | 6 |
| 11 | $^tBuCN$ | OTf | 1:3:2 | 74 (58)[b] |

[a]Reactions were performed with 0.1 mmol of 1-butyl-4-iodobenzene in 0.5 mL of DMF for 22 h. The yield was determined by $^{19}F$ NMR with 1-bromo-4-fluorobenzene as an internal standard added after the reaction.
[b]The reaction was conducted at 120° C. for 22 h.
ArI = 1; X = OTf; ($^tBuCN)_2$Cu OTf.

Example 2

Preparation of ($^tBuCN)_2CuOTf$

A similar procedure was used for the preparation of all nitrile ligated copper complexes reported in the manuscript. This procedure was carried out in a fumehood without any exclusion of moisture or oxygen until the product was isolated. 1.8 g $Cu_2O$ (12.6 mmol) and 20 mL of $^tBuCN$ were stirred vigorously in a 50 mL round bottom flask at room temperature. Trifluoromethanesulfonic acid (1.5 mL, 17 mmol) was added over 1 minute. The exothermic reaction was stirred for 5 minutes and quickly filtered through celite and rinsed with a small amount of diethyl ether. The clear, light orange filtrate was poured into 100 mL of diethyl ether and cooled to −20° C. White needles formed within 15 minutes and were collected on a fritted funnel under a blanket of nitrogen. The white needles were placed under vacuum (100 mtorr) at room temperature overnight. 4.3 grams (11.3 mmol) of white needles were obtained and were stored in an inert atmosphere.

Elemental Analysis Calc'd: C, 34.87; H, 4.79; N, 7.39. Found: C, 34.96; H, 4.88; N, 7.53.

Example 3A

Independent Synthesis of Authentic
N-(4-fluorophenyl)pivalamide (2n)

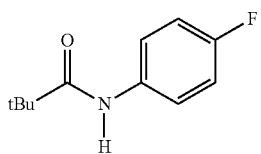 [SMILES: CC(C)(C)C(=O)Nc1ccc(F)cc1]

4-Fluoroaniline (947 μL, 10.0 mmol), 4-dimethylaminopyridine (DMAP, 12 mg, 0.1 mmol), and pyridine (1.6 mL, 20 mmol) were dissolved in 20 mL of $CH_2Cl_2$ and cooled to 0° C. Pivaloyl chloride (1.35 mL, 11.0 mmol) was added dropwise, and the resulting solution was allowed to warm to room temperature and stirred a total of 12 h. The solution was poured into a separatory funnel and washed with 1×20 mL of 1 M HCl and 1×20 mL of saturated $NaHCO_3$. The organic layer was dried with $MgSO_4$ and concentrated to afford a white solid (1.80 g, 9.2 mmol, 92% yield).

$^1$H NMR (600 MHz, $CDCl_3$) δ 7.47 (dd, J=7.7, 5.0 Hz, 2H), 7.30 (s, 1H), 7.01 (t, J=8.4 Hz, 2H), 1.31 (s, 9H).

$^{13}$C NMR (151 MHz, $CDCl_3$) δ 176.52 (s), 159.33 (d, J=243.4 Hz), 134.00 (d, J=2.7 Hz), 121.86 (d, J=7.9 Hz), 115.53 (d, J=22.4 Hz), 39.51 (s), 27.60 (s).

$^{19}$F NMR (376 MHz, $CDCl_3$) δ -122.20--122.38 (m).

Example 3B

Independent Synthesis of Authentic
N-(4-fluorophenyl)-N-methylpivalamide (2o)

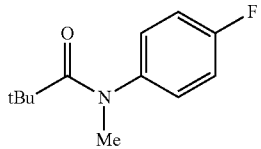 [SMILES: CN(C(=O)C(C)(C)C)c1ccc(F)cc1]

N-(4-Fluorophenyl)pivalamide (586 mg, 3.0 mmol) was dissolved in 3 mL of anhydrous THF, and the resulting solution was added dropwise to a suspension of 60% NaH (143 mg, 3.6 mmol) in 6 mL of anhydrous THF. The resulting solution was stirred at room temperature for 30 minutes, and methyl iodide (280 μL, 4.5 mmol) was added dropwise. After stirring for 2 h, water was added, and the product was extracted with ether. Drying with $MgSO_4$ and removal of the solvent gave 2o as a clear oil (581 mg, 2.8 mmol, 93% yield).

$^1$H NMR (600 MHz, $CDCl_3$) δ 7.21-7.16 (m, 2H), 7.07 (t, J=7.9 Hz, 2H), 3.19 (s, 3H), 1.04 (s, 9H).

$^{13}$C NMR (151 MHz, $CDCl_3$) δ 178.10 (s), 161.70 (d, J=248.1 Hz), 141.33 (d, J=2.5 Hz), 130.40 (d, J=8.5 Hz), 116.09 (d, J=22.6 Hz), 41.39 (s), 40.74 (s), 29.45 (s).

$^{19}$F NMR (376 MHz, $CDCl_3$) δ -116.28--116.50 (m).

Example 3C

Independent Synthesis of Authentic
1-(4-fluorobenzyl)-1H-indole (2p)

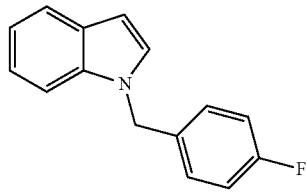 [SMILES: Fc1ccc(Cn2ccc3ccccc32)cc1]

Indole (352 mg, 3.0 mmol) and potassium hydroxide (202 mg, 3.6 mmol) were suspended in 3 mL of anhydrous DMF. 4-Fluorobenzyl bromide (374 μL, 3.0 mmol) was dissolved in 2 mL of anhydrous DMF, and the resulting solution was added dropwise. After stirring for 12 h, water was added, and the product was extracted with ether. Drying with $MgSO_4$ and removal of the solvent gave crude 2p. The product was purified by silica gel chromatography with 9:1 hexanes:ethyl acetate (R=0.64) to afford 2p as a clear oil (500 mg, 2.2 mmol, 74% yield).

$^1$H NMR (600 MHz, $CDCl_3$) δ 7.66 (d, J=7.8 Hz, 1H), 7.27 (d, J=6.6 Hz, 1H), 7.18 (t, J=7.6 Hz, 1H), 7.12 (t, J=7.4 Hz, 2H), 7.10-7.05 (m, 2H), 6.98 (t, J=8.5 Hz, 2H), 6.56 (d, J=3.0 Hz, 1H), 5.30 (s, 2H).

$^{13}$C NMR (151 MHz, $CDCl_3$) δ 162.22 (d, J=245.9 Hz), 136.17 (s), 133.25 (d, J=3.2 Hz), 128.77 (s), 128.41 (d, J=8.1 Hz), 128.03 (s), 121.77 (s), 121.04 (s), 119.62 (s), 115.65 (d, J=21.6 Hz), 109.56 (s), 101.88 (s), 49.41 (s).

$^{19}$F NMR (376 MHz, $CDCl_3$) δ -117.64--117.83 (m).

Example 4

General Procedure for the Fluorination of Aryl Iodides

To an oven-dried 4 mL vial was added AgF (25 mg, 0.2 mmol, 2.0 equiv), ($^t$BuCN)$_2$CuOTf (114 mg, 0.3 mmol, 3.0 equiv) and DMF (0.5 mL). Aryl iodide (0.1 mmol, 1.0 equiv) is added (solid aryl iodides were weighed in the vial prior to adding DMF, and liquid aryl iodides were added neat by syringe after the addition of DMF). The vial is sealed with a Teflon-lined cap and heated at 140° C. with vigorous stirring for 22 h. The solution is allowed to cool to room temperature and 11.0 μL (0.1 mmol, 1.0 equiv) of 1-bromo-4-fluorobenzene is added as an internal standard. The crude reaction mixture is analyzed by $^{19}$F NMR spectroscopy to determine the yield of aryl fluoride. $^{19}$F NMR chemical shifts were compared to authentic samples of the aryl fluoride product to confirm the identity of the product. The identities of the products were further confirmed by GC/MS.

Example 4A

Synthesis of 1-butyl-4-fluorobenzene (2a)

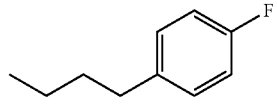

To an oven-dried 20 mL vial was added AgF (127 mg, 1.0 mmol, 2.0 equiv), (tBuCN)$_2$CuOTf (568 mg, 1.5 mmol, 3.0 equiv) and DMF (2.5 mL). 1-butyl-4-iodobenzene (89 µL, 1.0 mmol, 1.0 equiv) was added, and the reaction was heated at 140° C. for 22 h. The reaction was cooled, diluted with 15 mL of ether and filtered through Celite. The organic layer was washed with water (5×15 mL) and brine (1×15 mL). The organic layer was dried with MgSO$_4$, concentrated, and purified by silica gel chromatography eluting with hexanes to afford a clear oil (47 mg, 0.31 mmol, 62% yield).

$^1$H NMR (400 MHz, CDCl$_3$) δ 7.15-7.08 (m, 2H), 6.99-6.90 (m, 2H), 2.61-2.54 (m, 2H), 1.62-1.49 (m, 2H), 1.34 (dq, J=14.6, 7.3 Hz, 2H), 0.92 (t, J=7.3 Hz, 3H).
$^{13}$C NMR (151 MHz, CDCl$_3$) δ 161.13 (d, J=242.8 Hz), 138.43 (d, J=3.2 Hz), 129.63 (d, J=7.7 Hz), 114.88 (d, J=21.0 Hz), 34.81 (s), 33.75 (s), 22.23 (s), 13.90 (s).
$^{19}$F NMR (376 MHz, CDCl$_3$) δ −120.52--−120.61 (m).

Example 5

X-Ray Crystallographic Analysis of (tBuCN)$_4$CuOTf

A colorless needle 0.15×0.06×0.04 mm in size was mounted on a Cryoloop with Paratone oil. Data were collected in a nitrogen gas stream at 100(2) K using phi and omega scans. Crystal-to-detector distance was 40 mm and exposure time was 10 seconds per frame using a scan width of 0.5°. Data collection was 99.5% complete to 25.00° in θ. A total of 31958 reflections were collected covering the indices, −13<=h<=15, −13<=k<=13, −26<=l<=26. 5926 reflections were found to be symmetry independent, with an R$_{int}$ of 0.0310. Indexing and unit cell refinement indicated a primitive, monoclinic lattice. The space group was found to be P2(1)/n (No. 14). The data were integrated using the Bruker SAINT software program and scaled using the SADABS software program. Solution by direct methods (SIR-2011) produced a complete heavy-atom phasing model consistent with the proposed structure. All non-hydrogen atoms were refined anisotropically by full-matrix least-squares (SHELXL-97). All hydrogen atoms were placed using a riding model. Their positions were constrained relative to their parent atom using the appropriate HFIX command in SHELXL-97.

| | |
|---|---|
| Empirical formula | C$_{25}$H$_{46}$CuF$_3$N$_4$O$_4$S |
| Formula weight | 619.26 |
| Temperature | 100(2) K |
| Wavelength | 0.71073 Å |
| Crystal system | Monoclinic |
| Space group | P2(1)/n |
| Unit cell dimensions | a = 12.965(4) Å  α = 90°. |
| | b = 11.375(3) Å  β = 91.863(14)°. |
| | c = 22.117(7) Å  γ = 90°. |
| Volume | 3259.8(17) Å$^3$ |
| Z | 4 |
| Density (calculated) | 1.262 Mg/m$^3$ |
| Absorption coefficient | 0.784 mm$^{-1}$ |
| F(000) | 1312 |
| Crystal size | 0.15 × 0.06 × 0.04 mm$^3$ |
| Crystal color/habit | colorless needle |
| Theta range for data collection | 1.80 to 25.47°. |
| Index ranges | −13 <= h <= 15, −13 <= k <= 13, −26 <= l <= 26 |
| Reflections collected | 31958 |
| Independent reflections | 5926 [R(int) = 0.0310] |
| Completeness to theta = 25.00° | 99.5% |
| Absorption correction | Semi-empirical from equivalents |
| Max. and min. transmission | 0.9693 and 0.8914 |
| Refinement method | Full-matrix least-squares on F$^2$ |
| Data/restraints/parameters | 5926/0/357 |
| Goodness-of-fit on F$^2$ | 1.043 |
| Final R indices [I > 2sigma(I)] | R1 = 0.0257, wR2 = 0.0632 |
| R indices (all data) | R1 = 0.0335, wR2 = 0.0671 |
| Largest diff. peak and hole | 0.305 and −0.350 e · Å$^{-3}$ |

TABLE 2

Atomic coordinates (×10$^4$) and equivalent isotropic displacement parameters (Å$^2$ × 10$^3$). U(eq) is defined as one third of the trace of the orthogonalized U$^{ij}$ tensor.

| | x | y | z | U(eq) |
|---|---|---|---|---|
| C(1) | 7746(1) | 4042(1) | 6351(1) | 15(1) |
| C(2) | 7869(1) | 4759(1) | 5796(1) | 16(1) |
| C(3) | 7092(1) | 4336(2) | 5308(1) | 24(1) |
| C(4) | 7680(1) | 6054(1) | 5958(1) | 23(1) |
| C(5) | 8979(1) | 4604(2) | 5588(1) | 24(1) |
| C(6) | 9513(1) | 1060(1) | 7843(1) | 15(1) |
| C(7) | 10421(1) | 303(1) | 7985(1) | 16(1) |
| C(8) | 10133(1) | −968(2) | 7816(1) | 28(1) |
| C(9) | 10691(1) | 410(2) | 8667(1) | 28(1) |
| C(10) | 11324(1) | 724(2) | 7608(1) | 25(1) |
| C(11) | 5713(1) | 744(1) | 7324(1) | 15(1) |
| C(12) | 4802(1) | −13(1) | 7184(1) | 15(1) |
| C(13) | 3880(1) | 808(1) | 7072(1) | 19(1) |
| C(14) | 5015(1) | −732(2) | 6610(1) | 20(1) |
| C(15) | 4611(1) | −826(1) | 7724(1) | 20(1) |
| C(16) | 7005(1) | 4298(1) | 8597(1) | 15(1) |
| C(17) | 6795(1) | 5083(1) | 9117(1) | 17(1) |
| C(18) | 6446(1) | 4308(2) | 9646(1) | 25(1) |
| C(19) | 5941(1) | 5952(2) | 8932(1) | 24(1) |
| C(20) | 7797(1) | 5730(2) | 9294(1) | 26(1) |
| C(21) | 3934(1) | 2210(2) | 8908(1) | 23(1) |
| C(22) | 9044(1) | 2824(2) | 10450(1) | 26(1) |
| C(23) | 9607(2) | 2516(2) | 9882(1) | 35(1) |
| C(24) | 7443(1) | 2562(1) | 10927(1) | 21(1) |
| C(25) | 6406(1) | 1983(2) | 10839(1) | 24(1) |
| N(1) | 7656(1) | 3486(1) | 6781(1) | 18(1) |
| N(2) | 8806(1) | 1634(1) | 7731(1) | 17(1) |
| N(3) | 6391(1) | 1370(1) | 7417(1) | 17(1) |
| N(4) | 7184(1) | 3670(1) | 8206(1) | 16(1) |
| O(1) | 2650(1) | 3181(1) | 8153(1) | 26(1) |
| O(2) | 2234(1) | 3139(1) | 9222(1) | 33(1) |
| O(3) | 3595(1) | 4424(1) | 8873(1) | 30(1) |
| O(4) | 8072(1) | 2243(1) | 10434(1) | 21(1) |
| F(1) | 3504(1) | 1144(1) | 8846(1) | 38(1) |
| F(2) | 4353(1) | 2265(1) | 9470(1) | 37(1) |
| F(3) | 4706(1) | 2259(1) | 8521(1) | 38(1) |
| S(1) | 2991(1) | 3378(1) | 8773(1) | 18(1) |
| Cu(1) | 7521(1) | 2551(1) | 7542(1) | 13(1) |

TABLE 3

Bond lengths [Å] and angles [°].

| | | | |
|---|---|---|---|
| C(1)-N(1) | 1.151(2) | C(13)-H(13B) | 0.9800 |
| C(1)-C(2) | 1.487(2) | C(13)-H(13C) | 0.9800 |
| C(2)-C(3) | 1.529(2) | C(14)-H(14A) | 0.9800 |
| C(2)-C(5) | 1.535(2) | C(14)-H(14B) | 0.9800 |
| C(2)-C(4) | 1.538(2) | C(14)-H(14C) | 0.9800 |
| C(3)-H(3A) | 0.9800 | C(15)-H(15A) | 0.9800 |
| C(3)-H(3B) | 0.9800 | C(15)-H(15B) | 0.9800 |
| C(3)-H(3C) | 0.9800 | C(15)-H(15C) | 0.9800 |
| C(4)-H(4A) | 0.9800 | C(16)-N(4) | 1.151(2) |
| C(4)-H(4B) | 0.9800 | C(16)-C(17) | 1.488(2) |
| C(4)-H(4C) | 0.9800 | C(17)-C(19) | 1.530(2) |
| C(5)-H(5A) | 0.9800 | C(17)-C(20) | 1.533(2) |
| C(5)-H(5B) | 0.9800 | C(17)-C(18) | 1.544(2) |
| C(5)-H(5C) | 0.9800 | C(18)-H(18A) | 0.9800 |
| C(6)-N(2) | 1.146(2) | C(18)-H(18B) | 0.9800 |
| C(6)-C(7) | 1.484(2) | C(18)-H(18C) | 0.9800 |
| C(7)-C(10) | 1.536(2) | C(19)-H(19A) | 0.9800 |
| C(7)-C(8) | 1.537(2) | C(19)-H(19B) | 0.9800 |

TABLE 3-continued

Bond lengths [Å] and angles [°].

| | | | |
|---|---|---|---|
| C(7)-C(9) | 1.541(2) | C(19)-H(19C) | 0.9800 |
| C(8)-H(8A) | 0.9800 | C(20)-H(20A) | 0.9800 |
| C(8)-H(8B) | 0.9800 | C(20)-H(20B) | 0.9800 |
| C(8)-H(8C) | 0.9800 | C(20)-H(20C) | 0.9800 |
| C(9)-H(9A) | 0.9800 | C(21)-F(1) | 1.339(2) |
| C(9)-H(9B) | 0.9800 | C(21)-F(3) | 1.339(2) |
| C(9)-H(9C) | 0.9800 | C(21)-F(2) | 1.342(2) |
| C(10)-H(10A) | 0.9800 | C(21)-S(1) | 1.8237(18) |
| C(10)-H(10B) | 0.9800 | C(22)-O(4) | 1.422(2) |
| C(10)-H(10C) | 0.9800 | C(22)-C(23) | 1.514(3) |
| C(11)-N(3) | 1.145(2) | C(22)-H(22A) | 0.9900 |
| C(11)-C(12) | 1.485(2) | C(22)-H(22B) | 0.9900 |
| C(12)-C(13) | 1.531(2) | C(23)-H(23A) | 0.9800 |
| C(12)-C(15) | 1.536(2) | C(23)-H(23B) | 0.9800 |
| C(12)-C(14) | 1.543(2) | C(23)-H(23C) | 0.9800 |
| C(13)-H(13A) | 0.9800 | C(24)-O(4) | 1.429(2) |
| C(24)-C(25) | 1.505(2) | N(2)-Cu(1) | 1.9981(14) |
| C(24)-H(24A) | 0.9900 | N(3)-Cu(1) | 2.0006(14) |
| C(24)-H(24B) | 0.9900 | N(4)-Cu(1) | 2.0023(14) |
| C(25)-H(25A) | 0.9800 | O(1)-S(1) | 1.4440(13) |
| C(25)-H(25B) | 0.9800 | O(2)-S(1) | 1.4442(13) |
| C(25)-H(25C) | 0.9800 | O(3)-S(1) | 1.4372(13) |
| N(1)-Cu(1) | 2.0037(15) | | |
| N(1)-C(1)-C(2) | 179.65(17) | C(10)-C(7)-C(8) | 110.13(14) |
| C(1)-C(2)-C(3) | 108.90(13) | C(6)-C(7)-C(9) | 108.41(13) |
| C(1)-C(2)-C(5) | 108.10(13) | C(10)-C(7)-C(9) | 110.65(14) |
| C(3)-C(2)-C(5) | 110.76(14) | C(8)-C(7)-C(9) | 110.99(15) |
| C(1)-C(2)-C(4) | 108.08(13) | C(7)-C(8)-H(8A) | 109.5 |
| C(3)-C(2)-C(4) | 111.13(14) | C(7)-C(8)-H(8B) | 109.5 |
| C(5)-C(2)-C(4) | 109.76(14) | H(8A)-C(8)-H(8B) | 109.5 |
| C(2)-C(3)-H(3A) | 109.5 | C(7)-C(8)-H(8C) | 109.5 |
| C(2)-C(3)-H(3B) | 109.5 | H(8A)-C(8)-H(8C) | 109.5 |
| H(3A)-C(3)-H(3B) | 109.5 | H(8B)-C(8)-H(8C) | 109.5 |
| C(2)-C(3)-H(3C) | 109.5 | C(7)-C(9)-H(9A) | 109.5 |
| H(3A)-C(3)-H(3C) | 109.5 | C(7)-C(9)-H(9B) | 109.5 |
| H(3B)-C(3)-H(3C) | 109.5 | H(9A)-C(9)-H(9B) | 109.5 |
| C(2)-C(4)-H(4A) | 109.5 | C(7)-C(9)-H(9C) | 109.5 |
| C(2)-C(4)-H(4B) | 109.5 | H(9A)-C(9)-H(9C) | 109.5 |
| H(4A)-C(4)-H(4B) | 109.5 | H(9B)-C(9)-H(9C) | 109.5 |
| C(2)-C(4)-H(4C) | 109.5 | C(7)-C(10)-H(10A) | 109.5 |
| H(4A)-C(4)-H(4C) | 109.5 | C(7)-C(10)-H(10B) | 109.5 |
| H(4B)-C(4)-H(4C) | 109.5 | H(10A)-C(10)-H(10B) | 109.5 |
| C(2)-C(5)-H(5A) | 109.5 | C(7)-C(10)-H(10C) | 109.5 |
| C(2)-C(5)-H(5B) | 109.5 | H(10A)-C(10)-H(10C) | 109.5 |
| H(5A)-C(5)-H(5B) | 109.5 | H(10B)-C(10)-H(10C) | 109.5 |
| C(2)-C(5)-H(5C) | 109.5 | N(3)-C(11)-C(12) | 176.77(16) |
| H(5A)-C(5)-H(5C) | 109.5 | C(11)-C(12)-C(13) | 106.93(13) |
| H(5B)-C(5)-H(5C) | 109.5 | C(11)-C(12)-C(15) | 109.60(13) |
| N(2)-C(6)-C(7) | 179.29(17) | C(13)-C(12)-C(15) | 110.37(13) |
| C(6)-C(7)-C(10) | 108.54(13) | C(11)-C(12)-C(14) | 108.42(13) |
| C(6)-C(7)-C(8) | 108.05(13) | C(13)-C(12)-C(14) | 110.43(13) |
| C(15)-C(12)-C(14) | 110.99(13) | H(19A)-C(19)-H(19C) | 109.5 |
| C(12)-C(13)-H(13A) | 109.5 | H(19B)-C(19)-H(19C) | 109.5 |
| C(12)-C(13)-H(13B) | 109.5 | C(17)-C(20)-H(20A) | 109.5 |
| H(13A)-C(13)-H(13B) | 109.5 | C(17)-C(20)-H(20B) | 109.5 |
| C(12)-C(13)-H(13C) | 109.5 | H(20A)-C(20)-H(20B) | 109.5 |
| H(13A)-C(13)-H(13C) | 109.5 | C(17)-C(20)-H(20C) | 109.5 |
| H(13B)-C(13)-H(13C) | 109.5 | H(20A)-C(20)-H(20C) | 109.5 |
| C(12)-C(14)-H(14A) | 109.5 | H(20B)-C(20)-H(20C) | 109.5 |
| C(12)-C(14)-H(14B) | 109.5 | F(1)-C(21)-F(3) | 106.88(14) |
| H(14A)-C(14)-H(14B) | 109.5 | F(1)-C(21)-F(2) | 106.97(14) |
| C(12)-C(14)-H(14C) | 109.5 | F(3)-C(21)-F(2) | 107.55(14) |
| H(14A)-C(14)-H(14C) | 109.5 | F(1)-C(21)-S(1) | 111.61(12) |
| H(14B)-C(14)-H(14C) | 109.5 | F(3)-C(21)-S(1) | 112.05(13) |
| C(12)-C(15)-H(15A) | 109.5 | F(2)-C(21)-S(1) | 111.48(12) |
| C(12)-C(15)-H(15B) | 109.5 | O(4)-C(22)-C(23) | 108.77(14) |
| H(15A)-C(15)-H(15B) | 109.5 | O(4)-C(22)-H(22A) | 109.9 |
| C(12)-C(15)-H(15C) | 109.5 | C(23)-C(22)-H(22A) | 109.9 |
| H(15A)-C(15)-H(15C) | 109.5 | O(4)-C(22)-H(22B) | 109.9 |
| H(15B)-C(15)-H(15C) | 109.5 | C(23)-C(22)-H(22B) | 109.9 |
| N(4)-C(16)-C(17) | 178.03(17) | H(22A)-C(22)-H(22B) | 108.3 |
| C(16)-C(17)-C(19) | 109.23(14) | C(22)-C(23)-H(23A) | 109.5 |
| C(16)-C(17)-C(20) | 108.14(13) | C(22)-C(23)-H(23B) | 109.5 |
| C(19)-C(17)-C(20) | 110.99(14) | H(23A)-C(23)-H(23B) | 109.5 |
| C(16)-C(17)-C(18) | 107.96(13) | C(22)-C(23)-H(23C) | 109.5 |
| C(19)-C(17)-C(18) | 110.16(14) | H(23A)-C(23)-H(23C) | 109.5 |
| C(20)-C(17)-C(18) | 110.28(14) | H(23B)-C(23)-H(23C) | 109.5 |
| C(17)-C(18)-H(18A) | 109.5 | O(4)-C(24)-C(25) | 108.68(13) |
| C(17)-C(18)-H(18B) | 109.5 | O(4)-C(24)-H(24A) | 110.0 |
| H(18A)-C(18)-H(18B) | 109.5 | C(25)-C(24)-H(24A) | 110.0 |
| C(17)-C(18)-H(18C) | 109.5 | O(4)-C(24)-H(24B) | 110.0 |
| H(18A)-C(18)-H(18C) | 109.5 | C(25)-C(24)-H(24B) | 110.0 |
| H(18B)-C(18)-H(18C) | 109.5 | H(24A)-C(24)-H(24B) | 108.3 |
| C(17)-C(19)-H(19A) | 109.5 | C(24)-C(25)-H(25A) | 109.5 |
| C(17)-C(19)-H(19B) | 109.5 | C(24)-C(25)-H(25B) | 109.5 |
| H(19A)-C(19)-H(19B) | 109.5 | H(25A)-C(25)-H(25B) | 109.5 |
| C(17)-C(19)-H(19C) | 109.5 | C(24)-C(25)-H(25C) | 109.5 |
| H(25A)-C(25)-H(25C) | 109.5 | | |
| H(25B)-C(25)-H(25C) | 109.5 | | |
| C(1)-N(1)-Cu(1) | 178.48(13) | | |
| C(6)-N(2)-Cu(1) | 176.60(13) | | |
| C(11)-N(3)-Cu(1) | 175.75(13) | | |
| C(16)-N(4)-Cu(1) | 178.37(13) | | |
| C(22)-O(4)-C(24) | 112.92(13) | | |
| O(3)-S(1)-O(1) | 115.02(7) | | |
| O(3)-S(1)-O(2) | 115.42(8) | | |
| O(1)-S(1)-O(2) | 115.39(8) | | |
| O(3)-S(1)-C(21) | 102.66(8) | | |
| O(1)-S(1)-C(21) | 103.03(8) | | |
| O(2)-S(1)-C(21) | 102.54(8) | | |
| N(2)-Cu(1)-N(3) | 106.28(6) | | |
| N(2)-Cu(1)-N(4) | 112.22(6) | | |
| N(3)-Cu(1)-N(4) | 110.56(6) | | |
| N(2)-Cu(1)-N(1) | 110.98(5) | | |
| N(3)-Cu(1)-N(1) | 108.95(6) | | |
| N(4)-Cu(1)-N(1) | 107.82(6) | | |

TABLE 4

Anisotropic displacement parameters ($Å^2 \times 10^3$).
The anisotropic displacement factor exponent takes the form: $-2\pi^2[h^2a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(1) | 13(1) | 15(1) | 18(1) | -3(1) | 1(1) | 1(1) |
| C(2) | 19(1) | 15(1) | 13(1) | 2(1) | 2(1) | 1(1) |
| C(3) | 30(1) | 26(1) | 17(1) | 2(1) | -3(1) | -4(1) |
| C(4) | 36(1) | 17(1) | 17(1) | 2(1) | 4(1) | 3(1) |
| C(5) | 23(1) | 29(1) | 20(1) | 5(1) | 7(1) | 4(1) |
| C(6) | 17(1) | 15(1) | 14(1) | -2(1) | 4(1) | -4(1) |
| C(7) | 14(1) | 15(1) | 20(1) | -2(1) | 0(1) | 2(1) |
| C(8) | 22(1) | 18(1) | 44(1) | -4(1) | -4(1) | 3(1) |
| C(9) | 27(1) | 33(1) | 24(1) | 0(1) | -3(1) | 8(1) |
| C(10) | 17(1) | 27(1) | 31(1) | -1(1) | 6(1) | 0(1) |
| C(11) | 17(1) | 15(1) | 13(1) | 1(1) | 3(1) | 3(1) |
| C(12) | 13(1) | 15(1) | 16(1) | -1(1) | 1(1) | -2(1) |
| C(13) | 16(1) | 20(1) | 21(1) | 0(1) | 0(1) | -1(1) |
| C(14) | 18(1) | 22(1) | 19(1) | -4(1) | 2(1) | -2(1) |
| C(15) | 21(1) | 18(1) | 21(1) | 2(1) | 2(1) | -4(1) |
| C(16) | 15(1) | 14(1) | 17(1) | 4(1) | 1(1) | -1(1) |
| C(17) | 21(1) | 15(1) | 15(1) | -3(1) | 2(1) | 0(1) |
| C(18) | 37(1) | 22(1) | 16(1) | 1(1) | 6(1) | 0(1) |
| C(19) | 28(1) | 19(1) | 24(1) | -3(1) | 4(1) | 4(1) |
| C(20) | 25(1) | 27(1) | 25(1) | -9(1) | 2(1) | -4(1) |
| C(21) | 23(1) | 25(1) | 22(1) | 4(1) | 2(1) | 1(1) |
| C(22) | 21(1) | 32(1) | 26(1) | -3(1) | 0(1) | -6(1) |
| C(23) | 26(1) | 48(1) | 30(1) | -5(1) | 6(1) | -4(1) |
| C(24) | 26(1) | 21(1) | 17(1) | -2(1) | -1(1) | 2(1) |
| C(25) | 27(1) | 24(1) | 21(1) | 1(1) | 4(1) | -2(1) |
| N(1) | 19(1) | 17(1) | 17(1) | 1(1) | 3(1) | 1(1) |
| N(2) | 17(1) | 18(1) | 17(1) | 0(1) | 3(1) | -1(1) |
| N(3) | 16(1) | 17(1) | 17(1) | 1(1) | 2(1) | 0(1) |
| N(4) | 18(1) | 15(1) | 16(1) | 1(1) | 1(1) | 0(1) |
| O(1) | 29(1) | 26(1) | 22(1) | 0(1) | -8(1) | 2(1) |
| O(2) | 28(1) | 42(1) | 30(1) | 3(1) | 12(1) | 5(1) |
| O(3) | 41(1) | 18(1) | 30(1) | -2(1) | -6(1) | -6(1) |
| O(4) | 20(1) | 23(1) | 21(1) | -5(1) | 2(1) | -2(1) |
| F(1) | 48(1) | 16(1) | 51(1) | 3(1) | 2(1) | 2(1) |
| F(2) | 38(1) | 47(1) | 27(1) | 13(1) | -11(1) | 3(1) |
| F(3) | 27(1) | 49(1) | 39(1) | 10(1) | 13(1) | 14(1) |

TABLE 4-continued

Anisotropic displacement parameters (Å$^2$ × 10$^3$).
The anisotropic displacement factor exponent takes
the form: $-2\pi^2[h^2a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| S(1) | 19(1) | 16(1) | 17(1) | −1(1) | 0(1) | 2(1) |
| Cu(1) | 14(1) | 13(1) | 13(1) | 0(1) | 1(1) | 0(1) |

TABLE 5

Hydrogen coordinates (×10$^4$) and isotropic
displacement parameters (Å$^2$ × 10$^3$).

| | x | y | z | U(eq) |
|---|---|---|---|---|
| H(3A) | 7255 | 3525 | 5195 | 37 |
| H(3B) | 7131 | 4844 | 4951 | 37 |
| H(3C) | 6394 | 4369 | 5464 | 37 |
| H(4A) | 6982 | 6142 | 6108 | 35 |
| H(4B) | 7754 | 6544 | 5598 | 35 |
| H(4C) | 8185 | 6301 | 6273 | 35 |
| H(5A) | 9463 | 4882 | 5906 | 36 |
| H(5B) | 9074 | 5061 | 5218 | 36 |
| H(5C) | 9108 | 3771 | 5507 | 36 |
| H(8A) | 9556 | −1227 | 8058 | 42 |
| H(8B) | 10729 | −1482 | 7896 | 42 |
| H(8C) | 9932 | −1006 | 7385 | 42 |
| H(9A) | 10868 | 1227 | 8764 | 42 |
| H(9B) | 11281 | −99 | 8770 | 42 |
| H(9C) | 10096 | 169 | 8899 | 42 |
| H(10A) | 11123 | 696 | 7178 | 37 |
| H(10B) | 11922 | 211 | 7685 | 37 |
| H(10C) | 11505 | 1532 | 7722 | 37 |
| H(13A) | 3753 | 1255 | 7441 | 29 |
| H(13B) | 3268 | 342 | 6961 | 29 |
| H(13C) | 4030 | 1353 | 6743 | 29 |
| H(14A) | 5113 | −195 | 6270 | 29 |
| H(14B) | 4427 | −1250 | 6517 | 29 |
| H(14C) | 5639 | −1206 | 6678 | 29 |
| H(15A) | 5211 | −1338 | 7794 | 30 |
| H(15B) | 3998 | −1308 | 7636 | 30 |
| H(15C) | 4502 | −351 | 8085 | 30 |
| H(18A) | 5808 | 3896 | 9526 | 37 |
| H(18B) | 6323 | 4805 | 9998 | 37 |
| H(18C) | 6986 | 3733 | 9749 | 37 |
| H(19A) | 6161 | 6419 | 8586 | 35 |
| H(19B) | 5805 | 6475 | 9272 | 35 |
| H(19C) | 5311 | 5518 | 8817 | 35 |
| H(20A) | 8337 | 5156 | 9399 | 38 |
| H(20B) | 7680 | 6238 | 9644 | 38 |
| H(20C) | 8014 | 6211 | 8954 | 38 |
| H(22A) | 9457 | 2572 | 10812 | 32 |
| H(22B) | 8942 | 3685 | 10474 | 32 |
| H(23A) | 9700 | 1662 | 9861 | 52 |
| H(23B) | 10283 | 2902 | 9892 | 52 |
| H(23C) | 9202 | 2785 | 9527 | 52 |
| H(24A) | 7360 | 3426 | 10941 | 25 |
| H(24B) | 7774 | 2301 | 11314 | 25 |
| H(25A) | 6086 | 2238 | 10454 | 36 |
| H(25B) | 5962 | 2206 | 11171 | 36 |
| H(25C) | 6492 | 1127 | 10836 | 36 |

Example 6

X-Ray Crystallographic Analysis of ($^t$BuCN)$_2$CuOTf

A colorless needle 0.06×0.05×0.03 mm in size was mounted on a Cryoloop with Paratone oil. Data were collected in a nitrogen gas stream at 100(2) K using phi and omega scans. Crystal-to-detector distance was 40 mm and exposure time was 5 seconds per frame using a scan width of 0.5°. Data collection was 100.0% complete to 25.00° in θ. A total of 13340 reflections were collected covering the indices, −11<=h<=11, −12<=k<=10, −21<=l<=17. 2993 reflections were found to be symmetry independent, with an R$_{int}$ of 0.0300. Indexing and unit cell refinement indicated a primitive, orthorhombic lattice. The space group was found to be P2(1)2(1)2(1) (No. 19). The data were integrated using the Bruker SAINT software program and scaled using the SADABS software program. Solution by direct methods (SIR-2011) produced a complete heavy-atom phasing model consistent with the proposed structure. All non-hydrogen atoms were refined anisotropically by full-matrix least-squares (SHELXL-97). All hydrogen atoms were placed using a riding model. Their positions were constrained relative to their parent atom using the appropriate HFIX command in SHELXL-97.

| | |
|---|---|
| Empirical formula | C$_{11}$H$_{18}$CuF$_3$N$_2$O$_3$S |
| Formula weight | 378.87 |
| Temperature | 100(2) K |
| Wavelength | 0.71073 Å |
| Crystal system | Orthorhombic |
| Space group | P2(1)2(1)2(1) |
| Unit cell dimensions | a = 9.2021(3) Å  α = 90°. |
| | b = 10.0062(4) Å  β = 90°. |
| | c = 17.8241(6) Å  γ = 90°. |
| Volume | 1641.21(10) Å$^3$ |
| Z | 4 |
| Density (calculated) | 1.533 Mg/m$^3$ |
| Absorption coefficient | 1.497 mm$^{-1}$ |
| F(000) | 776 |
| Crystal size | 0.06 × 0.05 × 0.03 mm$^3$ |
| Crystal color/habit | colorless needle |
| Theta range for data collection | 2.29 to 25.37°. |
| Index ranges | −11 <= h <= 11, −12 <= k <= 10, −21 <= l <= 17 |
| Reflections collected | 13340 |
| Independent reflections | 2993 [R(int) = 0.0300] |
| Completeness to theta = 25.00° | 100.0% |
| Absorption correction | Semi-empirical from equivalents |
| Max. and min. transmission | 0.9565 and 0.9156 |
| Refinement method | Full-matrix least-squares on F$^2$ |
| Data/restraints/parameters | 2993/0/196 |
| Goodness-of-fit on F$^2$ | 1.025 |
| Final R indices [I > 2sigma(I)] | R1 = 0.0227, wR2 = 0.0516 |
| R indices (all data) | R1 = 0.0250, wR2 = 0.0526 |
| Absolute structure parameter | −0.011(10) |
| Largest diff. peak and hole | 0.230 and −0.210 e · Å$^{-3}$ |

TABLE 6

Atomic coordinates (×10$^4$) and equivalent isotropic
displacement parameters (Å$^2$ × 10$^3$).
U(eq) is defined as one third of the
trace of the orthogonalized U$^{ij}$ tensor.

| | x | y | z | U(eq) |
|---|---|---|---|---|
| C(1) | 9232(2) | 6179(2) | 7378(1) | 16(1) |
| C(2) | 10772(2) | 6150(2) | 7135(1) | 18(1) |
| C(3) | 11234(3) | 4706(2) | 6998(2) | 31(1) |
| C(4) | 11695(2) | 6780(3) | 7757(1) | 24(1) |
| C(5) | 10878(3) | 6968(3) | 6411(1) | 31(1) |
| C(6) | 4588(2) | 8273(2) | 9068(1) | 15(1) |
| C(7) | 3866(3) | 9074(2) | 9658(1) | 20(1) |
| C(8) | 2576(3) | 9804(3) | 9308(2) | 41(1) |
| C(9) | 4954(3) | 10106(3) | 9947(2) | 40(1) |
| C(10) | 3405(4) | 8149(3) | 10289(2) | 52(1) |
| C(11) | 3585(3) | 3932(2) | 9077(1) | 21(1) |
| N(1) | 8046(2) | 6246(2) | 7562(1) | 18(1) |
| N(2) | 5154(2) | 7650(2) | 8619(1) | 18(1) |
| O(1) | 4880(2) | 4714(2) | 7870(1) | 18(1) |
| O(2) | 4975(2) | 2351(2) | 8195(1) | 19(1) |
| O(3) | 6365(2) | 3967(2) | 8922(1) | 27(1) |
| F(1) | 2328(1) | 3723(2) | 8725(1) | 31(1) |
| F(2) | 3647(2) | 3079(2) | 9649(1) | 37(1) |

TABLE 6-continued

Atomic coordinates (×10$^4$) and equivalent isotropic displacement parameters (Å$^2$ × 10$^3$). U(eq) is defined as one third of the trace of the orthogonalized U$^{ij}$ tensor.

|      | x       | y       | z       | U(eq)  |
|------|---------|---------|---------|--------|
| F(3) | 3551(2) | 5163(1) | 9362(1) | 32(1)  |
| S(1) | 5136(1) | 3721(1) | 8448(1) | 16(1)  |
| Cu(1)| 6101(1) | 6623(1) | 7861(1) | 16(1)  |

TABLE 7

Bond lengths [Å] and angles [°].

| | | | |
|---|---|---|---|
| C(1)-N(1) | 1.142(3) | C(8)-H(8B) | 0.9800 |
| C(1)-C(2) | 1.482(3) | C(8)-H(8C) | 0.9800 |
| C(2)-C(3) | 1.526(3) | C(9)-H(9A) | 0.9800 |
| C(2)-C(5) | 1.531(3) | C(9)-H(9B) | 0.9800 |
| C(2)-C(4) | 1.532(3) | C(9)-H(9C) | 0.9800 |
| C(3)-H(3A) | 0.9800 | C(10)-H(10A) | 0.9800 |
| C(3)-H(3B) | 0.9800 | C(10)-H(10B) | 0.9800 |
| C(3)-H(3C) | 0.9800 | C(10)-H(10C) | 0.9800 |
| C(4)-H(4A) | 0.9800 | C(11)-F(2) | 1.331(3) |
| C(4)-H(4B) | 0.9800 | C(11)-F(3) | 1.333(3) |
| C(4)-H(4C) | 0.9800 | C(11)-F(1) | 1.333(3) |
| C(5)-H(5A) | 0.9800 | C(11)-S(1) | 1.827(2) |
| C(5)-H(5B) | 0.9800 | N(1)-Cu(1) | 1.905(2) |
| C(5)-H(5C) | 0.9800 | N(2)-Cu(1) | 1.908(2) |
| C(6)-N(2) | 1.140(3) | O(1)-S(1) | 1.4496(17) |
| C(6)-C(7) | 1.480(3) | O(1)-Cu(1) | 2.2169(15) |
| C(7)-C(10) | 1.518(4) | O(2)-S(1) | 1.4509(16) |
| C(7)-C(8) | 1.526(4) | O(2)-Cu(1)#1 | 2.2481(16) |
| C(7)-C(9) | 1.528(4) | O(3)-S(1) | 1.4334(17) |
| C(8)-H(8A) | 0.9800 | Cu(1)-O(2)#2 | 2.2481(16) |
| N(1)-C(1)-C(2) | 177.3(3) | H(4A)-C(4)-H(4B) | 109.5 |
| C(1)-C(2)-C(3) | 109.4(2) | C(2)-C(4)-H(4C) | 109.5 |
| C(1)-C(2)-C(5) | 107.26(19) | H(4A)-C(4)-H(4C) | 109.5 |
| C(3)-C(2)-C(5) | 110.7(2) | H(4B)-C(4)-H(4C) | 109.5 |
| C(1)-C(2)-C(4) | 108.1(2) | C(2)-C(5)-H(5A) | 109.5 |
| C(3)-C(2)-C(4) | 110.54(19) | C(2)-C(5)-H(5B) | 109.5 |
| C(5)-C(2)-C(4) | 110.7(2) | H(5A)-C(5)-H(5B) | 109.5 |
| C(2)-C(3)-H(3A) | 109.5 | C(2)-C(5)-H(5C) | 109.5 |
| C(2)-C(3)-H(3B) | 109.5 | H(5A)-C(5)-H(5C) | 109.5 |
| H(3A)-C(3)-H(3B) | 109.5 | H(5B)-C(5)-H(5C) | 109.5 |
| C(2)-C(3)-H(3C) | 109.5 | N(2)-C(6)-C(7) | 179.3(2) |
| H(3A)-C(3)-H(3C) | 109.5 | C(6)-C(7)-C(10) | 108.8(2) |
| H(3B)-C(3)-H(3C) | 109.5 | C(6)-C(7)-C(8) | 108.53(19) |
| C(2)-C(4)-H(4A) | 109.5 | C(10)-C(7)-C(8) | 112.2(3) |
| C(2)-C(4)-H(4B) | 109.5 | C(6)-C(7)-C(9) | 108.1(2) |
| C(10)-C(7)-C(9) | 110.2(2) | F(2)-C(11)-F(1) | 107.26(19) |
| C(8)-C(7)-C(9) | 108.9(2) | F(3)-C(11)-F(1) | 107.68(19) |
| C(7)-C(8)-H(8A) | 109.5 | F(2)-C(11)-S(1) | 111.29(16) |
| C(7)-C(8)-H(8B) | 109.5 | F(3)-C(11)-S(1) | 111.01(16) |
| H(8A)-C(8)-H(8B) | 109.5 | F(1)-C(11)-S(1) | 111.78(17) |
| C(7)-C(8)-H(8C) | 109.5 | C(1)-N(1)-Cu(1) | 171.9(2) |
| H(8A)-C(8)-H(8C) | 109.5 | C(6)-N(2)-Cu(1) | 179.4(2) |
| H(8B)-C(8)-H(8C) | 109.5 | S(1)-O(1)-Cu(1) | 120.87(9) |
| C(7)-C(9)-H(9A) | 109.5 | S(1)-O(2)-Cu(1)#1 | 127.66(9) |
| C(7)-C(9)-H(9B) | 109.5 | O(3)-S(1)-O(1) | 115.45(10) |
| H(9A)-C(9)-H(9B) | 109.5 | O(3)-S(1)-O(2) | 115.19(10) |
| C(7)-C(9)-H(9C) | 109.5 | O(1)-S(1)-O(2) | 114.22(9) |
| H(9A)-C(9)-H(9C) | 109.5 | O(3)-S(1)-C(11) | 103.55(11) |
| H(9B)-C(9)-H(9C) | 109.5 | O(1)-S(1)-C(11) | 103.31(10) |
| C(7)-C(10)-H(10A) | 109.5 | O(2)-S(1)-C(11) | 102.71(11) |
| C(7)-C(10)-H(10B) | 109.5 | N(1)-Cu(1)-N(2) | 137.21(8) |
| H(10A)-C(10)-H(10B) | 109.5 | N(1)-Cu(1)-O(1) | 107.92(7) |
| C(7)-C(10)-H(10C) | 109.5 | N(2)-Cu(1)-O(1) | 103.15(7) |
| H(10A)-C(10)-H(10C) | 109.5 | N(1)-Cu(1)-O(2)#2 | 104.09(7) |
| H(10B)-C(10)-H(10C) | 109.5 | N(2)-Cu(1)-O(2)#2 | 102.54(7) |
| F(2)-C(11)-F(3) | 107.61(19) | O(1)-Cu(1)-O(2)#2 | 93.56(6) |

Symmetry transformations used to generate equivalent atoms:
1 −x + 1, y − 1/2, −z + 3/2
2 −x + 1, y + 1/2, −z + 3/2

TABLE 8

Anisotropic displacement parameters (Å$^2$ × 10$^3$) for hartwig07. The anisotropic displacement factor exponent takes the form: $-2\pi^2[h^2 a^{*2} U^{11} + \ldots + 2 h k a^* b^* U^{12}]$

|       | U$^{11}$ | U$^{22}$ | U$^{33}$ | U$^{23}$ | U$^{13}$ | U$^{12}$ |
|-------|--------|--------|--------|--------|--------|--------|
| C(1)  | 21(1)  | 15(1)  | 12(1)  | 0(1)   | −1(1)  | −1(1)  |
| C(2)  | 11(1)  | 22(1)  | 20(1)  | −1(1)  | 2(1)   | 0(1)   |
| C(3)  | 20(1)  | 31(1)  | 40(2)  | −12(1) | 1(1)   | 4(1)   |
| C(4)  | 17(1)  | 27(1)  | 27(1)  | −7(1)  | −2(1)  | −1(1)  |
| C(5)  | 25(1)  | 46(2)  | 22(1)  | 9(1)   | 4(1)   | −9(1)  |
| C(6)  | 15(1)  | 16(1)  | 14(1)  | 1(1)   | −2(1)  | −1(1)  |
| C(7)  | 24(1)  | 21(1)  | 14(1)  | −4(1)  | −2(1)  | 3(1)   |
| C(8)  | 33(2)  | 58(2)  | 33(2)  | −24(2) | −11(1) | 21(2)  |
| C(9)  | 41(2)  | 32(2)  | 48(2)  | −21(1) | −12(2) | 7(1)   |
| C(10) | 89(3)  | 36(2)  | 32(2)  | 0(2)   | 37(2)  | 6(2)   |
| C(11) | 28(1)  | 17(1)  | 18(1)  | 0(1)   | 3(1)   | 1(1)   |
| N(1)  | 20(1)  | 19(1)  | 14(1)  | 2(1)   | −1(1)  | −1(1)  |
| N(2)  | 18(1)  | 20(1)  | 16(1)  | −1(1)  | 1(1)   | −2(1)  |
| O(1)  | 21(1)  | 17(1)  | 16(1)  | −1(1)  | −2(1)  | −2(1)  |
| O(2)  | 22(1)  | 18(1)  | 16(1)  | −3(1)  | −1(1)  | 1(1)   |
| O(3)  | 24(1)  | 28(1)  | 29(1)  | −7(1)  | −12(1) | 3(1)   |
| F(1)  | 21(1)  | 39(1)  | 32(1)  | −2(1)  | 5(1)   | −3(1)  |
| F(2)  | 62(1)  | 32(1)  | 17(1)  | 7(1)   | 10(1)  | 4(1)   |
| F(3)  | 42(1)  | 21(1)  | 34(1)  | −10(1) | 14(1)  | 1(1)   |
| S(1)  | 16(1)  | 16(1)  | 15(1)  | −3(1)  | −2(1)  | 2(1)   |
| Cu(1) | 14(1)  | 20(1)  | 15(1)  | −2(1)  | 3(1)   | 0(1)   |

TABLE 5

Hydrogen coordinates (×10$^4$) and isotropic displacement parameters (Å$^2$ × 10$^3$).

|        | x     | y     | z     | U(eq) |
|--------|-------|-------|-------|-------|
| H(3A)  | 11032 | 4171  | 7446  | 46    |
| H(3B)  | 12277 | 4676  | 6887  | 46    |
| H(3C)  | 10691 | 4342  | 6571  | 46    |
| H(4A)  | 11403 | 7713  | 7828  | 35    |
| H(4B)  | 12723 | 6743  | 7615  | 35    |
| H(4C)  | 11549 | 6286  | 8226  | 35    |
| H(5A)  | 10243 | 6576  | 6029  | 47    |
| H(5B)  | 11884 | 6963  | 6231  | 47    |
| H(5C)  | 10575 | 7890  | 6511  | 47    |
| H(8A)  | 2922  | 10388 | 8904  | 62    |
| H(8B)  | 2089  | 10343 | 9692  | 62    |
| H(8C)  | 1891  | 9150  | 9103  | 62    |
| H(9A)  | 5798  | 9646  | 10161 | 60    |
| H(9B)  | 4492  | 10657 | 10334 | 60    |
| H(9C)  | 5271  | 10677 | 9531  | 60    |
| H(10A) | 2714  | 7487  | 10096 | 78    |
| H(10B) | 2942  | 8672  | 10688 | 78    |
| H(10C) | 4261  | 7690  | 10491 | 78    |

What is claimed is:

1. A reaction mixture for fluorinating an aryl compound having a leaving group, said reaction mixture comprising:
   (i) said aryl compound that is optionally substituted at one or more positions with one or more substituents other than said leaving group, such that said one or more substituents are not joined to form a nitrogen-containing macrocycle with three amine moieties;
   (ii) a fluoride ion source; and
   (iii) a metal ion source having the formula $$(M^{+n})_s(L)_m(X^{-t})_q$$

wherein
M is the metal ion selected from the group consisting of Cr, Mn, Co, Cu and Ag;
L is an organic ligand;
X is an anion;
m is 1, 2 or 3; and n, s, t and q are independently 1, 2 or 3, such that (s×n)=(t×q), wherein the molar ratio of the metal ion source to fluoride ion source is 1 or more.

2. The reaction mixture according to claim 1, wherein said aryl compound having a leaving group is an aryl halide.

3. The reaction mixture according to claim 2, wherein said aryl compound having a leaving group is an aryl iodide.

4. The reaction mixture according to claim 3, wherein the metal ion is Cu+.

5. The mixture according to claim 4, wherein m is 1 and L is RCN.

6. The reaction mixture according to claim 5, wherein R is unsubstituted C1-C6 alkyl.

7. The reaction mixture according to claim 6, wherein R does not have an abstractable proton.

8. The reaction mixture according to claim 7, wherein R is t-butyl.

9. The reaction mixture according to claim 8, wherein X is selected from the group consisting of BF4, PF6, SbF6 OTf, triflimide (Tf2N), perchlorate, tetrakis(pentafluorophenyl)borate, tetrakis(3,5-bistrifluoromethylphenyl)borate, Al(OC(CF3)3)4, nonaflate, sulfate, fluorosulfonate and chlorosulfonate.

10. The reaction mixture according to claim 9, wherein said fluoride ion source is selected from the group consisting of AgF and CsF.

11. The reaction mixture according to claim 10, wherein said reaction mixture is anhydrous.

12. The reaction mixture according to claim 10, wherein the ratio of Cu to said fluoride ion source is 1 or greater than 1.

13. The reaction mixture according to claim 12, wherein said aryl iodide, said Cu source and said fluoride ion source are present in said reaction mixture in a ratio which is from about 1:2:1 to about 1:10:2.

14. The reaction mixture according to claim 1, wherein said aryl compound having a leaving group is further substituted with a member selected from the group consisting of amine, ether, amide, ester, bromo, chloro, protected alcohol and a combination thereof.

15. The reaction mixture according to claim 1, wherein said aryl compound having a leaving group has the formula

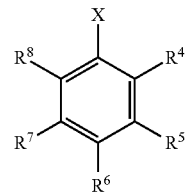

wherein
$R^4$, $R^5$, $R^6$, $R^7$, and $R^8$ are independently members selected from the group consisting of H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$, wherein two or more of $R^4$, $R^5$, $R^6$, $R^7$ and $R^8$, together with the atoms to which they are bonded, are optionally joined to form a ring system which is a member selected from the group consisting of substituted or unsubstituted cycloalkyl, substituted or unsubstituted heterocycloalkyl, substituted or unsubstituted aryl and substituted or unsubstituted heteroaryl, and $R^4$ and $R^8$ are not joined to form a nitrogen-containing macrocycle having three amine moieties, wherein
$R^9$ and $R^{10}$ are members independently selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from the group consisting of substituted or unsubstituted cycloalkyl, substituted or unsubstituted heterocycloalkyl, substituted or unsubstituted aryl and substituted or unsubstituted heteroaryl; and X is a leaving group.

16. A method for forming a fluoroaryl compound, said method comprising:
(a) forming a reaction mixture according to claim 1; and
(b) incubating said reaction mixture under conditions appropriate to form said fluoroaryl compound.

* * * * *